(12) United States Patent
Takaishi et al.

(10) Patent No.: US 6,261,248 B1
(45) Date of Patent: Jul. 17, 2001

(54) MAXILLARY TOOTH DIMENSION DETERMINING SYSTEM

(75) Inventors: Yoshitomo Takaishi, 66-1 Bozu-machi, Himeji, Hyogo-ken 670-0011 (JP); Shingo Furuoka, Himeji-shi (JP)

(73) Assignee: Yoshitomo Takaishi, Himeji (JP)

( * ) Notice: Subject to any disclaimer, the term of this patent is extended or adjusted under 35 U.S.C. 154(b) by 0 days.

(21) Appl. No.: 09/536,133

(22) Filed: Mar. 28, 2000

(30) Foreign Application Priority Data

Mar. 29, 1999 (JP) .................................................. 11-085580
Jul. 8, 1999 (JP) .................................................. 11-194246

(51) Int. Cl.[7] .................................................. A61B 5/103
(52) U.S. Cl. .............................. 600/590; 378/39; 382/118
(58) Field of Search .................................... 600/587, 590, 600/595; 382/118; 378/39

(56) References Cited

U.S. PATENT DOCUMENTS

| | | | |
|---|---|---|---|
| 3,610,227 | * 10/1971 | Griffin | 433/63 |
| 4,694,478 | * 9/1987 | Delnon | 378/39 |
| 5,482,048 | * 1/1996 | Johnson | 600/476 |
| 5,659,625 | * 8/1997 | Marquardt | 382/118 |
| 5,951,498 | * 9/1999 | Arnett | 600/587 |

\* cited by examiner

*Primary Examiner*—John P. Lacyk
*Assistant Examiner*—Pamela L. Wingood
(74) *Attorney, Agent, or Firm*—Duane, Morris & Heckscher LLP (57) ABSTRACT

A maxillary tooth dimension determining system includes a computer into which a photograph of a face of a client and its pupillary distance α are inputted. The width W1 and height H1 of the first maxillary incisors are computed in accordance with the following expression.

$$W1 = \alpha \times 2.5 \times (1/16) \text{ and}$$

$$H1 = W1 \times (4/3).$$

The width W2 of the second maxillary incisors is computed in accordance with the following expression.

$$W2 = 0.618 W1$$

An image of the teeth is displayed on a display screen together with the image of the client's face, in such a manner that it can be moved to an appropriate position in the image of the client's face.

16 Claims, 5 Drawing Sheets

MAXILLARY TOOTH DIMENSION DETERMINING SYSTEM

This invention relates to a system for use in esthetic dentistry for determining dimensions of maxillary teeth of a person so that the teeth match well his or her features.

BACKGROUND OF THE INVENTION

Cosmetic surgery is for improving a person's feature. One field of the cosmetic surgery is esthetic dentistry for improving the beauty of teeth. Esthetic dentistry improves the appearance of a tooth of a client by appropriate means, such as orthodontics, tooth extraction, putting in of an artificial tooth, moving of a tooth, removing of a portion of a tooth, bonding of prosthetic material to the remaining portion, and bonding of a prosthetic material to the front side or all sides of a tooth.

A reference used in esthetic dental treatment is dimensions of the first incisors in the maxilla. According to a conventional method, the height of the first incisors to be provided by esthetic dental treatment is 1/16 of the length of a face, and the width of the first incisors is 3/4 of its height. However, the facial length differs greatly from person to person, and the length of the face of a particular person greatly changes as she or he grows older. Accordingly, the determination of an appropriate height and width of the first maxillary incisors on the basis of the facial length is not always successful.

It has been thought to be most desirable to determine the widths of the first incisor, the second incisor and the canine tooth to be in the golden ratio, namely, 1.618:1.0:0.618. On the basis of such conception, sometimes it has been done to combine an image of a row of teeth in the golden section with image of the face of a client to prepare a composite image of his or her face, on which the widths of the teeth can be varied as desired. Then, the client can select the widths of the teeth she or he desires. However, by this method, the widths of the teeth best matching the client's feature cannot always be obtained.

The inventors have determined that the width of the maxillary incisors after the esthetic dental treatment should be determined on the basis of the length of the maxillary denture. When making the invention, the inventors took into account the fact that the length of the maxillary denture is related to the distance between the temporomandibular joints. However, it is difficult to accurately determine these dimensions with equipment installed in common dental clinics. According to the present invention, the distance between the temporomandibular joints is measured indirectly for use in determining the width of the maxillary incisors to be formed by esthetic dental treatment. Also, according to the present invention, dimensions of other teeth to be formed are determined on the basis of the determined width of the maxillary incisors.

SUMMARY OF THE INVENTION

According to a first embodiment of the present invention, the distance between the pupils of a client is measured by pupillary distance measuring means, and the measurement a is inputted into dimension determining means. The dimension determining means determines the dimensions of maxillary incisors from the measured pupillary distance $\alpha$. It may do the following computations to determined the width W1 and the height H1 of the first incisors.

$$W1 = \alpha \times 2.5 \times (1/16) \quad (1)$$

$$H1 = W1 \times (4/3) \quad (2)$$

The width W2 of the second incisors and the width W3 of the canine teeth are determined by the following equations in accordance with the golden section.

$$W2 = 0.618 W1 \quad (3)$$

$$W3 = 0.618 W2 = 0.618^2 W1 \quad (4)$$

An image of the face or its portion of the client is displayed on image display means. The image may be obtained by still image photographing means, e.g. an ordinary camera or a digital camera. An image of teeth having the temporarily determined dimensions as determined by the dimension determining means is displayed on the display means together with the image of the face or its portion. The position of the image of the teeth on the display means can be moved as desired, by display control means. For example, the image of the temporarily determined teeth can be superposed on the teeth in the photograph of the client's face. The dimension determining means and the display control means may be provided by, for example, the electronic computer, and the image display means may be a monitor associated with the computer. The pupillary distance measuring means may be ophthalmic scale or a spectacle adjustment optical meter. Alternatively, it may be realized by pointing the pupils displayed on the monitor by pointing means, e.g. a pointing device, and computing the distance between the pupils by the computer.

In esthetic dentistry, it is known to employ the height of first maxillary incisors which is equal to 1/16 of the length of a face as measured between the vertex and the tip of the lower jaw orthogonally projected onto a vertical plane, and the width which is equal to 3/4 of the height. The values "1/16" and "3/4" are for standard features. Since the ancient Greece, the width of an ideal face has been considered to be 3/4 of the length of the face. It is also known medically that the ideal pupillary distance is 1/2.5 of the ideal face width. Accordingly, the ideal feature includes a face width which is 2.5 times as large as the pupillary distance $\alpha$, a face length which is 4/3 times as long as the pupillary distance $\alpha$, and a maxillary incisor height H1 which is 1/16 times as large as the pupillary distance $\alpha$. Accordingly, the first incisor height H1 can be expressed as:

$$H1 = \alpha \times 2.5 \times 4/3 \times 1/16$$

The width W1 of the first maxillary incisors can be expressed as follows.

$$W1 = 3/4 \times H1 = \alpha \times 2.5 \times 1/16$$

As stated previously, the most important factor in determining the width of maxillary incisors is the distance between temporomandibular joints. The temporomandibular joint distance is dependent on the width of a cranium at the level of orbits. The orbits occupy almost the entire width of the cranium. The pupils are at the centers of the respective orbits. Accordingly, the temporomandibular joint distance can be known from the measured pupillary distance. Accordingly, the proper dimensions of the maxillary incisors can be determined without resort to a conventionally employed reference, e.g. the face length, which differs from person to person and also changes with age.

If the computed teeth dimensions do not fit the maxilla of the client in the displayed image, they can be modified on the display by means of the display control means through the pointing means. Usually, the amount of modification is within a range of from about −3% and to 0%, and does not go outside a range of from −10% to +3%. One or more of the above-described dental techniques are chosen for the treatment.

According to another embodiment of the present invention, a maxillary tooth dimension determining system may be realized, which can determine the thickness of maxillary teeth to be shaped. According to this embodiment, bottom still image information prepared by obtaining an image of a portion to be treated of a maxillary denture of a client from below by still image photographing means. At least right and left first and second incisors and right and left canines, for example, should be in the image.

The pupillary distance of a client is measured by pupillary distance measuring means, and information representing the measured pupillary distance is inputted into dimension determining means, which computes a temporarily determined width of the portion to be treated. The temporarily determined width may be, for example, the sum of at least the right and left first and second incisors and the canines. Display control means causes an image to be displayed on image display means. The displayed image is a bottom image of the portion of an ideal maxillary denture corresponding to the portion to be treated. The bottom image of the ideal denture is superimposed on the bottom still image of the portion of the maxillary denture of the client after being modified, if necessary, by magnifying or reducing it so that the width of the portion can be equal to the width of the portion of the client. The magnification or reduction is carried out through the display control means. The bottom image of the ideal maxillary denture portion to be displayed may be selected from a plurality of such images having different curvatures. The selected maxillary denture has a curvature approximating to that of the client's denture.

The bottom image of the ideal maxillary denture approximating to that of the client's as magnified or reduced so that its width can be equal to the width of the client's maxillary denture is the image of the aimed maxillary denture. The superimposition of the ideal denture bottom image on the bottom image of the actual maxillary denture of the client gives guidelines for modifying the thickness of a respective tooth in the maxillary denture should be modified.

The following modifications may be made to the above-described maxillary tooth dimension determining systems. A "client" apparatus may be installed at dental clinics, with a server apparatus installed at a different location. The client apparatuses are connected to the server apparatus via communications lines so as to enable communications therebetween. The Internet may be employed as the communications lines. Each client apparatus is provided with photographing means for obtaining a still image. The photographing means is used to obtain a front image of at least a maxillary tooth to be treated of a client. Pupillary distance measuring means may additionally be provided to measure the distance between pupils of the client. The maxillary tooth image information, or the maxillary tooth image information together with the measured pupillary distance information are transmitted to the server apparatus through the communications lines. Then, at the server apparatus, the temporarily determined dimensions of the maxillary teeth are determined from the pupillary distance information received from the pupillary distance measuring means or the pupillary distance information derived from the front image obtained by means of the photographing means. The server apparatus prepares a composite image formed by superimposing an image of the maxillary teeth having the temporarily determined dimensions on the location on the front image of the client where the maxillary teeth should be. The prepared composite image information to the appropriate client apparatus. At the client apparatus, the received composite image information is displayed on display means.

Alternatively, a plurality of client apparatuses, a server apparatus and communications lines may be used. Each client apparatus is provided with still image photographing means and pupillary distance measuring means. The still image photographing means is used to obtain a still image of a portion of a maxillary denture to be treated from below the face of a client and develops bottom still image information. The pupillary distance measuring means measures the distance between the two pupils of the client and develops pupillary distance information representative of the measured pupillary distance. The bottom still image information and the pupillary distance information are transmitted to the server apparatus via the communications lines. Dimension determining means at the server apparatus uses the received pupillary distance information transmitted from the client apparatus to determine the temporary length of the maxillary denture. The server apparatus includes combining means, which magnifies or reduces the size of a bottom image of an ideal maxillary denture to match the length of the ideal maxillary denture with the temporarily determined length, before developing ideal image information formed by combining the magnified or reduced image with the information of the photographed bottom still image. The server apparatus transmits the ideal image information back to the client apparatus. The client apparatus includes display means for displaying an image prepared from the received ideal image information.

Alternatively, the pupillary distance measuring means may be removed from the client apparatus, and the still image photographing means is arranged to provide, in addition to the bottom still image information, a still front image of at least one maxillary tooth of the client. The bottom and front image information is transmitted to the server apparatus via the communications lines. The dimension determining means at the server apparatus derives the pupillary distance information from the received still front image information and determines a temporary length of the maxillary denture from the derived pupillary distance information.

In a tooth dimension determining method according to the present invention, the client apparatus transmits to the server apparatus, tooth information for use in determining ideal dimensions of a tooth to be shaped of a client, and information of an image of the actual tooth to be shaped are transmitted through the communications lines. The server apparatus determines the ideal tooth dimensions, using the received tooth information. The server apparatus develops composite image information representative of a composite image prepared by processing the tooth information and the actual tooth image information in such a manner as to superpose the image of the ideal tooth having the determined ideal dimensions on the image of the actual tooth to be shaped. The server apparatus transmits the composite image information back to the client apparatus. The client apparatus processes the composite image information to develop an image of the ideal tooth substituted for the tooth to be shaped.

DETAILED DESCRIPTION OF EMBODIMENTS

Figure 1:
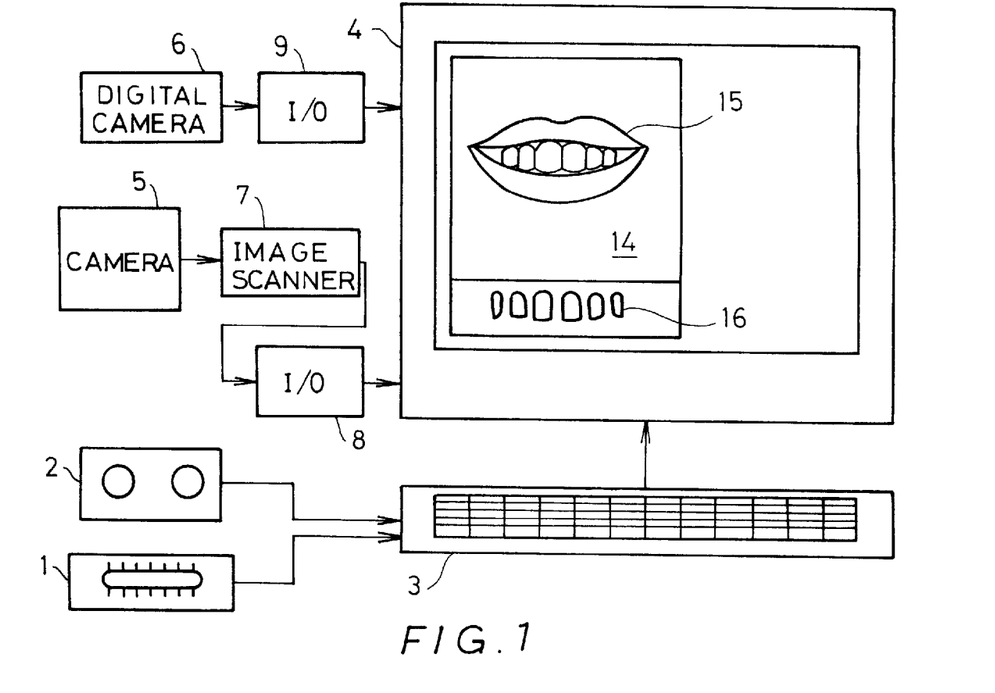
FIG. 1 is a block diagram of a maxillary tooth dimension determining system according to a first embodiment of the present invention.

FIG. 1 shows a system for determining dimensions of teeth in the maxilla of a client according to a first embodiment of the present invention. As stated previously, the present invention requires measurement of the pupillary distance α of the client with pupillary distance measuring means. For example, an ophthalmic scale 1 may be used to measure the pupillary distance α. It is, however, desirable to use, as the pupillary distance measuring means, an optical meter 2 for use in spectacle adjustment, e.g. PD Meter PM-600 available from Nidec Corporation. An optical meter 2 is not so expensive and, in addition, can make measurement with accuracy. The pupillary distance α thus measured is inputted through input means, e.g. a keyboard 3, to an electronic computer, e.g. a personal computer 4. An image of the face of the client is obtained by still image photographing means, e.g. an ordinary camera 5 or a digital camera 6. When the ordinary camera 5 is used, an image obtained is converted into electrical image information by means of an image scanner 7, and the resulting image information is inputted into the computer 4 through an interface (I/O) 8. If the client's face is photographed by the digital camera 6, image information from the camera 6 is inputted through an interface (I/O) 9 into the computer 4.

Figure 2:
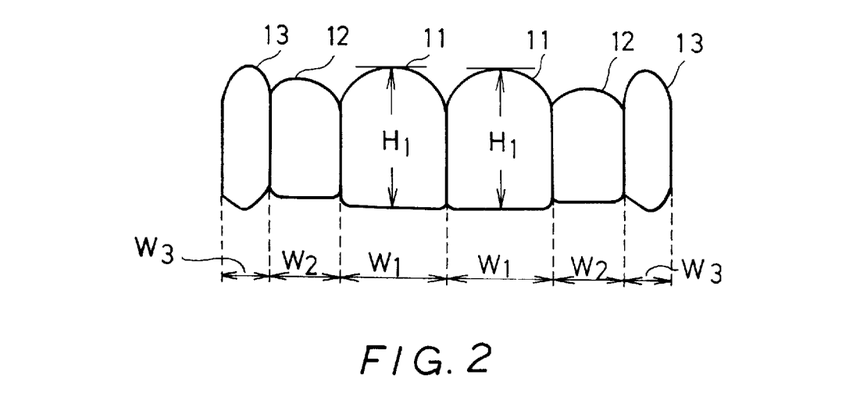
FIG. 2 is a front view of maxillary teeth whose widths are determined by the system shown in FIG. 1.

The computer 4 acts as dimension determining means and computes dimensions W1, W2, W3 and H1 of the first incisors 11, the second incisors 12 and the canines 13 shown in FIG. 2, in accordance with the following equations (1)–(4).

$$W1 = \alpha \times 2.5 \times (1/16) \quad (1)$$

$$H1 = W1 \times (4/3) \quad (2)$$

$$W2 = 0.618 W1 \quad (3)$$

$$W3 = 0.618 W2 = 0.618^2 W1 \quad (4)$$

The computer 4 controls a monitor provided therefor to display an image 15 of the face of the client or its part including the mouth on a display screen 14 of the monitor. Thus, the computer 4 functions as display control means. The computer 4 causes an image 16 of the teeth whose dimensions have been computed to be displayed on the screen 14 with the same magnification as the image 15.

A face looks most beautiful when a person smiles. In this case, the heights of the maxillary teeth appearing beneath the upper lip has a large factor in the beauty of the face. The height Hs of the portion of the first maxillary incisors appearing when she or he smiles should desirably has a relation to the entire height H1 expressed by the following equation (5).

$$Hs = H1 \times (2/3) \pm 2 \text{ mm} \quad (5)$$

The amount of correction expressed as ±2 mm is determined in accordance with the length of the face, the age of the client and other factors. The amount of correction is larger for a relatively long face, and it may be smaller for a relatively round face. For a face of an old person, the amount of correction may be smaller.

EXAMPLE 1

For a woman in her twenties who had a pupillary distance α=64 mm and wanted to have her first and second maxillary incisors treated:

W1=10.0 mm
W2=6.2 mm
H1=13.3 mm
Hs=9.3 mm (with correction of +0.4 mm made)

EXAMPLE 2

For a woman in her thirties who had a pupillary distance α=60 mm and wanted to have her first and second maxillary incisors and canines treated, and also for a woman in her twenties who had a pupillary distance α=60 mm and wanted to have her first and second maxillary incisors treated:

W1=9.4 mm
W2=5.8 mm
W3=3.8 mm
H1=12.5 mm
Hs=9.1 mm (with correction of +0.8 mm made)

EXAMPLE 3

For a man in his forties who had a pupillary distance α=66 mm and wanted to have his first and second maxillary incisors and canines treated:

W1=10.3 mm
W2=6.4 mm
W3=4.0 mm
H1=13.8 mm
Hs=9.7 mm (with correction of +0.5 mm made)

EXAMPLE 4

For a woman in her fifties who had a pupillary distance α=63 mm and wanted to have her first and second maxillary incisors and canines treated:

W1=9.8 mm
W2=6.1 mm
W3=3.8 mm
H1=13.1 mm
Hs=8.7 mm (with no correction made)

EXAMPLE 5

For a woman in her sixties who had a pupillary distance α=60 mm and wanted to have her first maxillary incisors treated:

W1=9.4 mm
H1=12.5 mm
Hs=8.0 mm (with correction of −0.3 mm made)

EXAMPLE 6

For a man in his seventies who had a pupillary distance α=60 mm and wanted to have his first maxillary incisors and one of his second maxillary incisors treated:

W1=9.4 mm
W2=5.8 mm
H1=12.5 mm

Hs=6.8 mm (with correction of −1.5 mm made)

The dentist, studying the line of maxillary occlusion, the tilt of each tooth, the mandibular denture etc. of each client, modifies, if necessary, the image 16 of the maxillary denture of each client so that the teeth to be treated can have the above-described dimensions. After that, the modified image 16 is substituted for the tooth portion of the client's face by changing the displayed position of the modified image 16. The dentist makes sure that the modified denture matches the other teeth before drawing up the plan for the treatment. The image 15 of the client's face with the image 16 of the modified teeth is presented to the client to ask her or him if it is satisfactory to her or him. With an agreement by the client, the dentist proceeds to treat the teeth.

Figure 3:
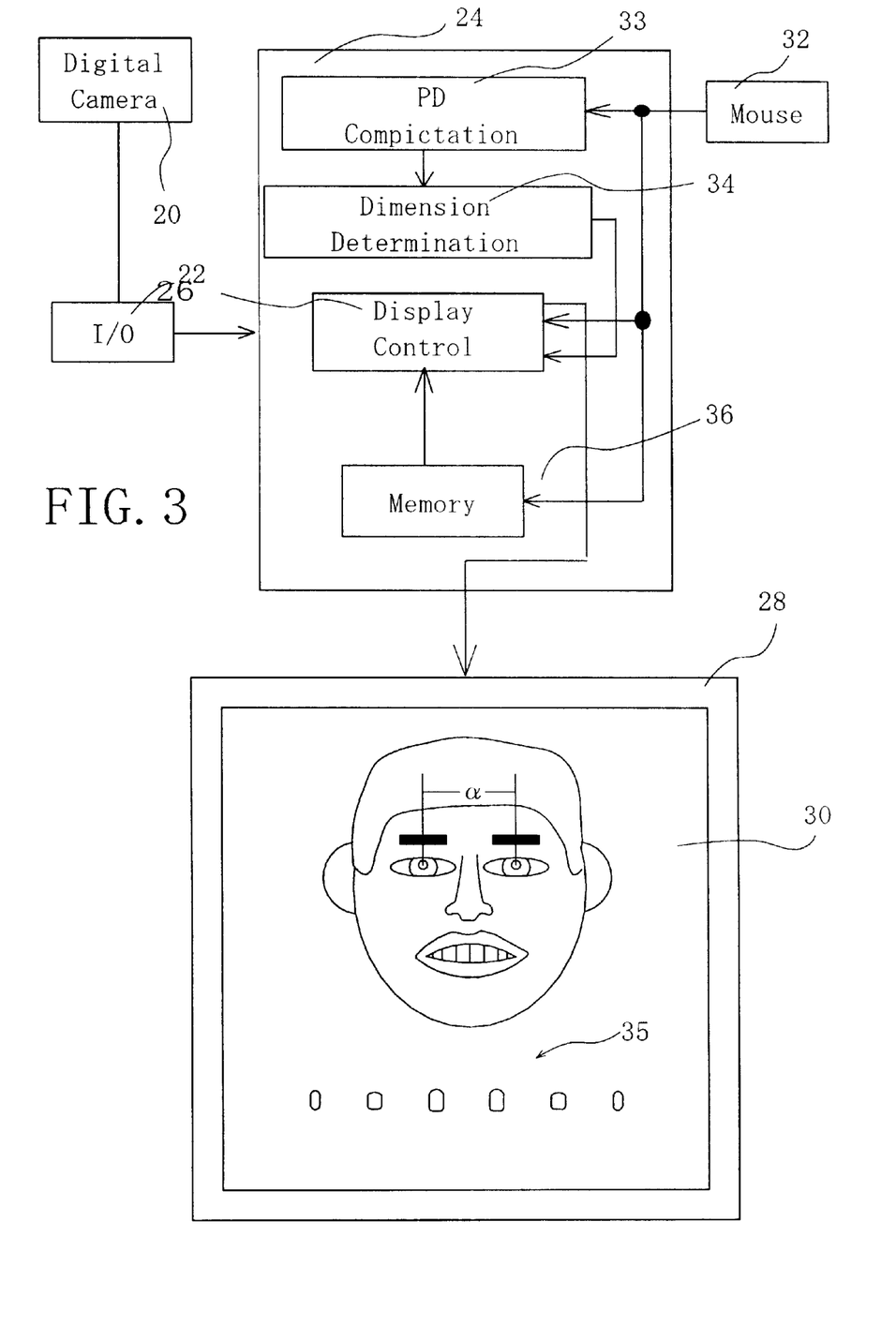
FIG. 3 is a block diagram of a maxillary tooth dimension determining system according to a second embodiment of the present invention.

A maxillary tooth dimension determining system according to a second embodiment of the invention is shown in FIG. 3. An image of a face of a client taken from the front of the face by still image photographing means, e.g. a digital camera 20 is inputted into an electronic computer, e.g. a personal computer 24 via an interface circuit 22. The computer 24 is programmed to realize the various functions described later. Display control means 26 provided in the computer 24 causes the inputted image to be displayed on display means, e.g. a monitor screen 30 of a monitor 28 provided for the computer 24.

Pointing means, e.g. a pointer device or, more specifically, a mouse 32 associated with the computer 24 is clicked at the locations where the pupils of the client are displayed. Pupillary distance (PD) computing means 33 in the computer 24 inputted with the clicked locations computes the pupillary distance α of the client. The pupillary distance α is inputted into dimension determining means 34 in the computer 24, which uses appropriate ones of the above-described expressions (1) through (4) to determine the dimensions of the maxillary teeth to be treated.

The determined dimensions are applied to the display control means 26 where an image of the teeth which would result from the treatment is prepared and displayed on the display screen 30. Also, the sum of the widths of the maxillary teeth to be treated has been computed.

In FIG. 3, an image 35 of the right and left first and second incisors and the right and left canines which would result from the treatment is displayed on the screen 30. The tilt and size of each tooth are adjusted on the image 35. Specifically, the image of the tooth to be adjusted is selected by clicking on it by the mouse 32, and the tilt and size of that tooth are modified through the mouse 32. The image of the adjusted tooth is displayed on the screen 30 by the display control means 26. The displayed image of the adjusted tooth is moved to the position for that tooth in the image 35 by the operation of the mouse 35 and substituted for the tooth before the adjustment.

Further, the digital camera 20 is used to obtain an image of the maxillary denture from its rear side, as shown in FIG. 4(*a*). The image information is transmitted to the personal computer 24 and is displayed on the monitor 28. The image should contain images of at least those teeth which are to be treated. For simplicity of illustration, only the teeth to be treated are shown in FIG. 4(*a*).

Figure 4A:
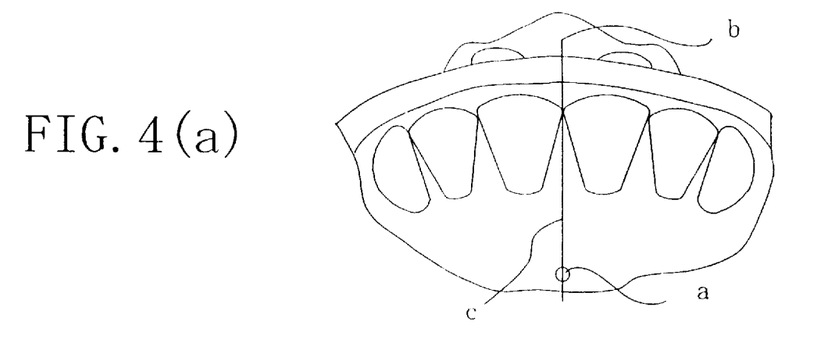
FIGS. 4(a) through 4(d) illustrate the sequence in which the thickness of a maxillary tooth is determined with the system shown in FIG. 3.
Figure 4B:
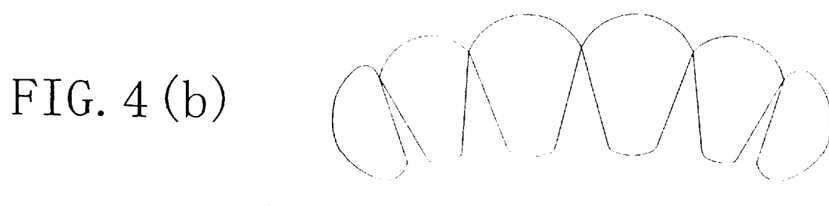
Figure 4C:
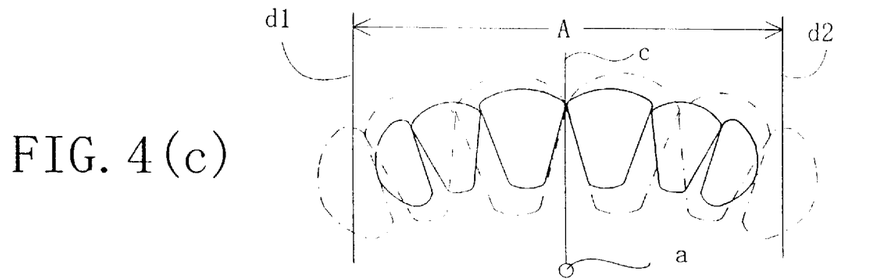

On the other hand, a plurality of images of maxillary dentures having different curvatures have been stored in maxillary denture memory means 36 in the personal computer 24. An image of a maxillary denture having a curvature similar to that of the maxillary denture of the client is selected from the plural images. For example, the images of the respective maxillary dentures are displayed on the screen 30 by means of the display control means 26, and one of the displayed images is selected by clicking on it with the mouse 32. FIG. 4(*b*) shows a selected image. For simplification of illustration, only an image portion corresponding to the portion to be treated is shown in FIG. 4(*b*).

The selected image is displayed on the monitor screen 30, being superposed on the image of the maxillary denture of the client, as shown in FIG. 4(*c*). The display control means 26 is used to superpose the images by moving the selected image, using the mouse 32. The incisor papilla "a" on the image of the client's maxillary denture displayed on the monitor screen 30 is clicked to prepare a reference for use in superposing the two images on each other. A point "b" through which a plumb line from the middle point of the pupillary distance "α" passes is then connected to the incisor papilla "a" displayed on the screen 30. The line "c" connecting the points "a" and "b" displayed on the screen 30 is the reference line. The selected image displayed on the screen 30 also contains the incisor papilla and the reference line, and the client's maxillary denture image is superposed on it with the reference line "c" and the incisor papilla "a" aligned with those of the selected image. FIG. 4(*c*) shows the superposed two maxillary denture images, in which the selected image is depicted by a dash-and-dot line.

Figure 4D:
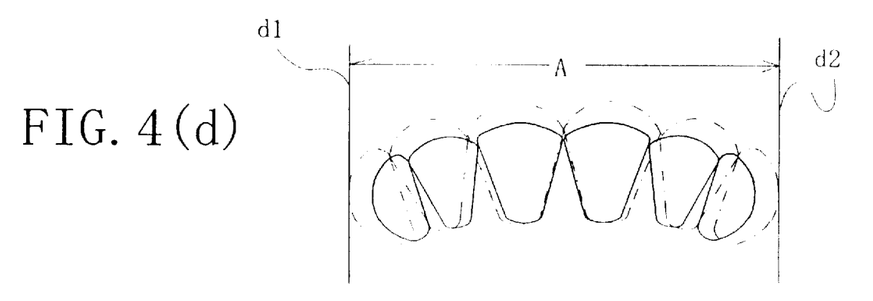

Next, boundaries d1 and d2 spaced by the width A of a portion of the maxillary denture of the client to be treated, as determined by the dimension determining means 34, are displayed on the screen 30 by the display control means 26, with the middle point of the width A placed on the reference line. Then, the selected image is enlarged or reduced in size by performing operations on the selected image by means of the mouse 32, so that the width of the selected image becomes equal to the width A, as shown in FIG. 4(*d*). Using the enlarged or reduced image and the client's maxillary denture image, the thickness of prosthetic material for the teeth to be treated can be determined.

Thus, it is possible to make the client visually recognize beforehand his or her mouth with the teeth having the widths and heights which would result from the treatment. Then, the client can receive the treatment, feeling at ease. Further, since the thickness of the prosthesis to be formed can be provided in the form of visual data, a dental technician can readily grasp the false teeth to be made. In addition, this can be realized readily, using a personal computer the dentist has now, without resort to any special equipment.

Figure 5A:
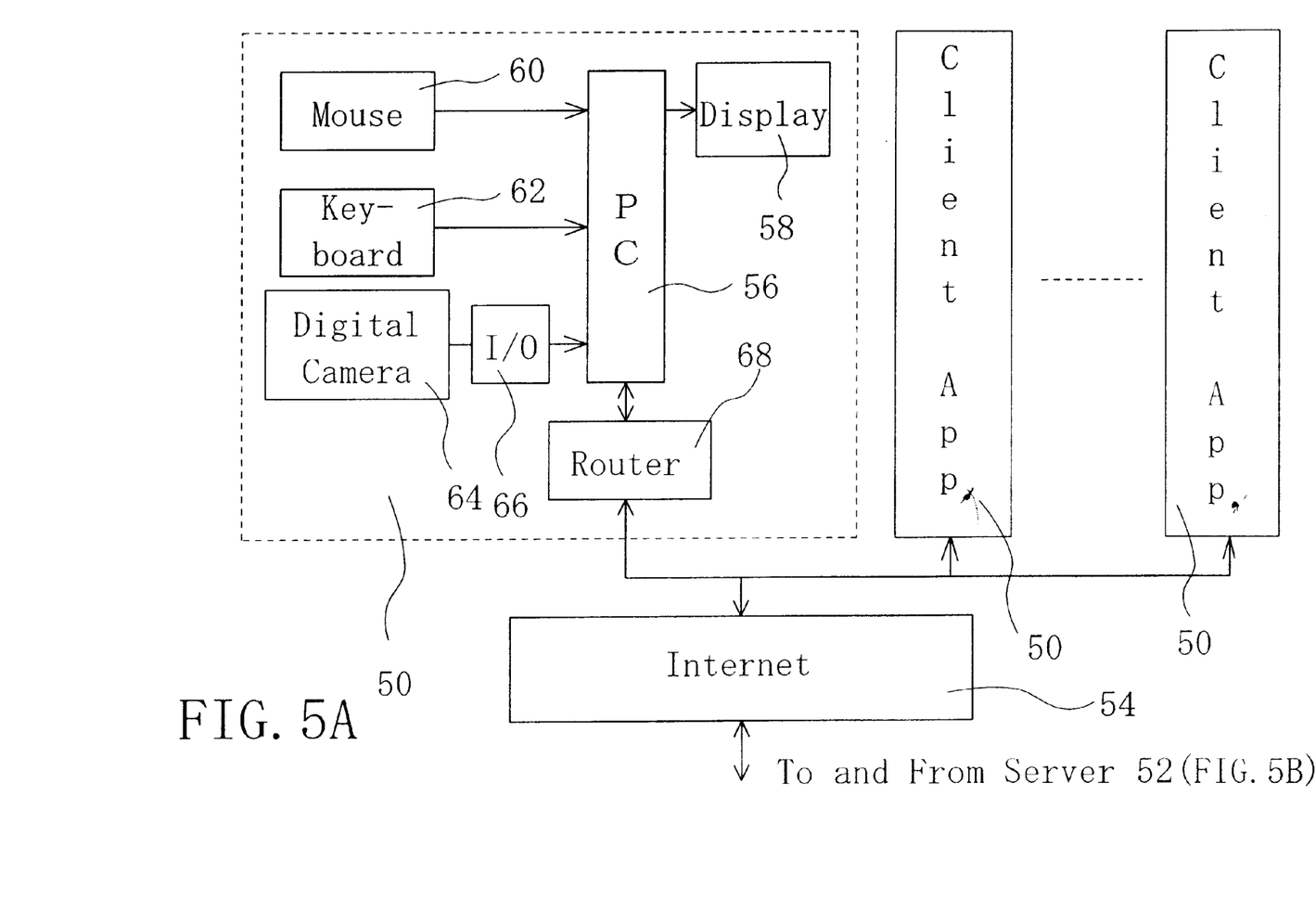
FIG. 5 is a block diagram of a maxillary tooth dimension determining system according to a third embodiment of the present invention.
Figure 5B:
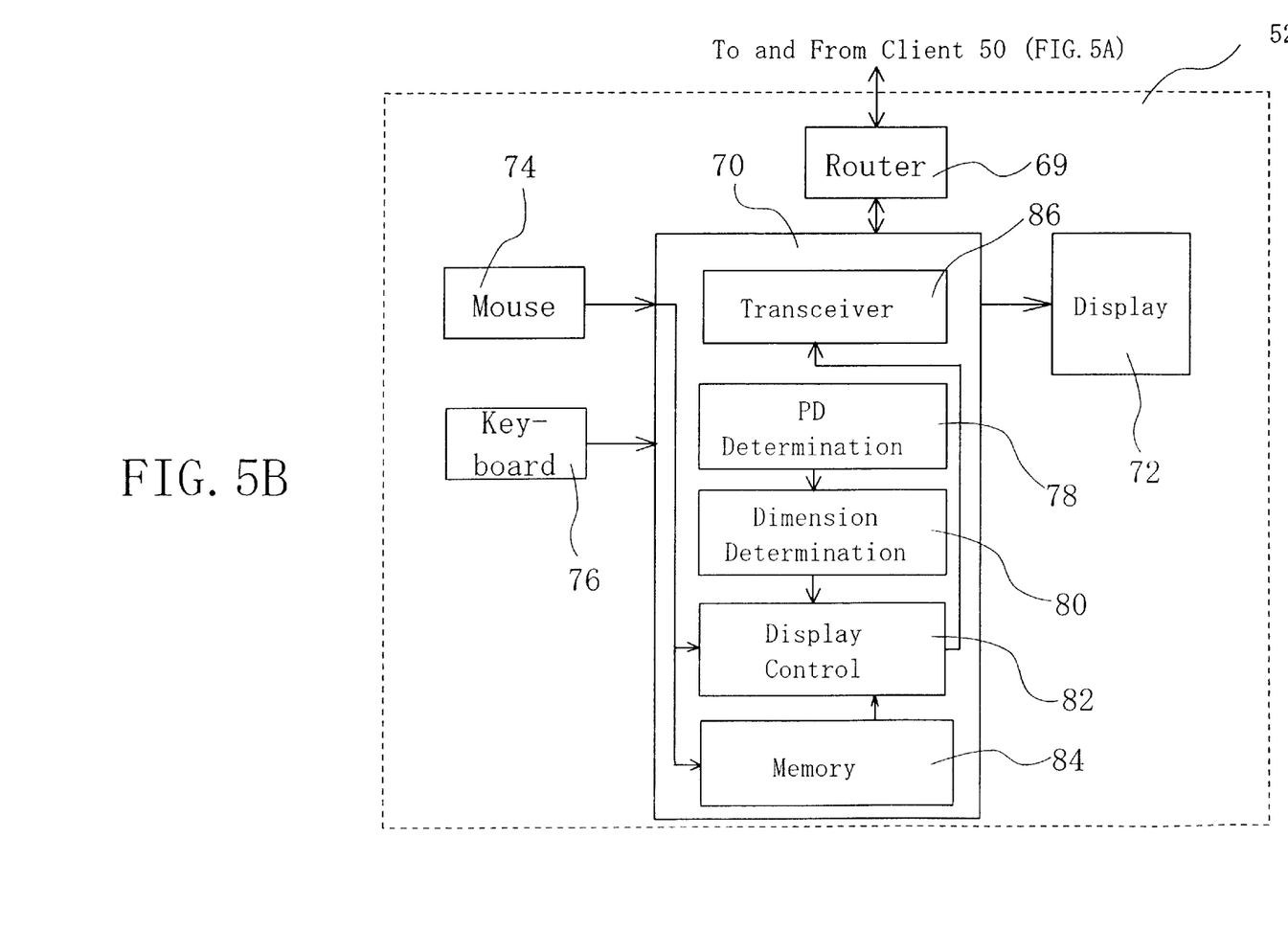

A maxillary tooth dimension determining system according to a third embodiment of the present invention is shown in FIG. 5. The system includes a plurality of client apparatuses 50 having the same configuration. Each client apparatus 50 is installed at one of dental clinics. A server apparatus 52 is provided at a location remote from the respective dental clinics. Each client apparatus 50 is connected to the server apparatus 52 by communications lines, e.g. Internet lines, 54.

Each client apparatus 50 includes a personal computer 56, and also a display 58, a mouse 60, a keyboard 62, a digital camera 64 and an interface circuit 66, which are all provided in association with the computer 56. The client apparatus 50 sends a picture of a client's face and a picture of a client mouth including the image of the maxillary denture to the server apparatus 52 through a router 66 and the Internet lines 54. As in the maxillary tooth dimension determining system according to the first embodiment, pictures taken by an ordinary camera can be sent to the server apparatus 52 after they are converted into digital information by means of an image scanner.

The server apparatus includes a personal computer 70 with a router 69 by which the computer 70 can connect with the Internet lines 54. The personal computer 70 is provided with a display 72, a mouse 74 and a keyboard 76. Like the personal computer of the maxillary tooth dimension determining system of the second embodiment described above, the personal computer 70 is so programmed as to be able to function as pupillary distance determining means 78, dimension determining means 80, display control means 82 and denture memory means 84. It is programmed to function also as transmitting/receiving (transceiver) means 86 for communications via the router 69.

Like the personal computer used in the maxillary tooth dimension determining system according to the second embodiment, the server apparatus 52 develops, by the display control means 82, image information representing the shapes of maxillary teeth after the treatment on the basis of the data sent to the server apparatus 52 from each client apparatus 50. The server apparatus 52 sends back the developed image information to the client apparatus 50 which sent the data to the server apparatus 52. In other words, the display control means 82 serves as the combining means.

The pupillary distance may be measured at a client apparatus 50. The result of measurement is then transmitted to the server apparatus 52.

The center between the pupils in a picture of a client's face may be clicked at a client apparatus 50 to transmit the picture with the specified center to the server apparatus 52.

The pupillary distance may be determined by means of a personal computer of a client apparatus 50, and the pupillary distance information is transmitted to the server apparatus 52.

By installing the client apparatus 50 at each of the dental clinics, the dental clinic has only to send the pupillary distance information to the server apparatus.

What is claimed is:

1. A maxillary tooth dimension determining system comprising:
    a camera;
    a pupillary distance measuring apparatus; and
    a computer receiving image information representative of a face of a client photographed by said camera and actual pupillary distance information representative of an actual distance between pupils of the client measured by said pupillary distance measuring apparatus;
    wherein:
        said computer computes an ideal dimension of a maxillary tooth, using said actual pupillary distance information, displays the face of the client or part thereof prepared in accordance with said image information on an image display device associated with said computer, and displays, on said image display device, an image of an ideal maxillary tooth having said ideal dimension in such a manner that the displayed image can have a size same as the displayed image of the face of the client or part thereof and can be moved to any location on said image display device.

2. A maxillary tooth dimension determining system comprising:
    still image photographing means for providing still image information representing a still image of at least a maxillary tooth of a client photographed from the front of a face of the client;
    pupillary distance measuring means for measuring a distance between pupils of the client and providing pupillary distance information representative of the measured pupillary distance;
    dimension determining means for computing an ideal width and ideal height of said maxillary tooth of the client, using said pupillary distance information as inputted thereto from said pupillary distance measuring means;
    image display means; and
    display control means for causing said still image to be displayed on said image display means, substituting image information representing an ideal maxillary tooth having the ideal width and height as determined by said dimension determining means for that part of said still image information which represents said maxillary tooth of the client to thereby provide composite image information representing a composite image comprising said still image combined with the ideal maxillary tooth, and causing said composite image to be displayed on said image display means.

3. A maxillary tooth dimension determining system comprising:
    a server apparatus, a plurality of client apparatuses, and communications links enabling communications between said server apparatus and said client apparatuses;
    wherein each of said client apparatuses comprises:
        still image photographing means for providing still image information representing a still image of at least a maxillary tooth of a client photographed from the front of a face of the client; and
        pupillary distance measuring means for measuring a distance between pupils of the client and providing pupillary distance information representing the measured pupillary distance;
        said still image representative information and said pupillary distance information being transmitted to said server apparatus through said communications links; and
    wherein said server apparatus comprises:
        dimension determining means for computing an ideal width and ideal height of said maxillary tooth, using said pupillary distance information as transmitted thereto from said client apparatus; and
        combining means for substituting image information representing an ideal maxillary tooth having the ideal width and height as determined by said dimension determining means for that part of said still image representative information which represents said maxillary tooth of the client, to thereby produce composite image information representing a composite image comprising said still image combined with said ideal maxillary tooth;
        said composite image information being transmitted to said client apparatus through said communications links; and
        said client apparatus further includes image display means for displaying said composite image based on said composite image information received through said communications links.

4. A maxillary tooth dimension determining system comprising:
    a server apparatus, a plurality of client apparatuses, and communications links enabling communications between said server apparatus and said client apparatuses;
    wherein each of said client apparatuses comprises still image photographing means for providing still image information representing a still image of at least a maxillary tooth of a client photographed from the front of a face of the client, and transmits said still image information to said server apparatus through said communications links;

said server apparatus comprises:
   dimension determining means for determining a distance between pupils of a client from said still image information transmitted through said communications links, providing pupillary distance information representing the determined distance, and computing an ideal width and ideal height of said maxillary tooth from said pupillary distance information; and
   combining means for substituting image information representing an ideal maxillary tooth having the ideal width and height as determined by said dimension determining means for that part of said still image information which represents said maxillary tooth of the client, to thereby produce composite image information representing a composite image comprising said still image combined with said ideal maxillary tooth;
   said server apparatus transmitting said composite image information to said client apparatus through said communications links; and
   said client apparatus further includes image display means for displaying said composite image based on said composite image information received through said communications links.

5. The maxillary tooth dimension determining system according to claim 1 wherein said maxillary tooth is a maxillary first incisor having a width W1 expressed as:

$$W1=\alpha \times 2.5 \times (1/16)$$

where $\alpha$ is said pupillary distance.

6. The maxillary tooth dimension determining system according to claim 2 wherein said maxillary tooth is a maxillary first incisor having a width W1 expressed as:

$$W1=\alpha \times 2.5 \times (1/16)$$

where $\alpha$ is said pupillary distance.

7. The maxillary tooth dimension determining system according to claim 3 wherein said maxillary tooth is a maxillary first incisor having a width W1 expressed as:

$$W1=\alpha \times 2.5 \times (1/16)$$

where $\alpha$ is said pupillary distance.

8. The maxillary tooth dimension determining system according to claim 4 wherein said maxillary tooth is a maxillary first incisor having a width W1 expressed as:

$$W1=\alpha \times 2.5 \times (1/16)$$

where $\alpha$ is said pupillary distance.

9. The maxillary tooth dimension determining system according to claim 1 wherein said maxillary tooth is a maxillary first incisor having a width W1 and a height H1;
   said width W1 is determined in accordance with an expression:

$$W1=\alpha \times 2.5 \times (1/16)$$

where $\alpha$ is said pupillary distance; and
   said height H1 is determined in accordance with an expression:

$$H1=W1 \times (4/3).$$

10. The maxillary tooth dimension determining system according to claim 2 wherein said maxillary tooth is a maxillary first incisor having a width W1 and a height H1;
   said width W1 is determined in accordance with an expression:

$$W1=\alpha \times 2.5 \times (1/16)$$

where $\alpha$ is said pupillary distance; and
   said height H1 is determined in accordance with an expression:

$$H1=W1 \times (4/3).$$

11. The maxillary tooth dimension determining system according to claim 3 wherein said maxillary tooth is a maxillary first incisor having a width W1 and a height H1;
   said width W1 is determined in accordance with an expression:

$$W1=\alpha \times 2.5 \times (1/16)$$

where $\alpha$ is said pupillary distance; and
   said height H1 is determined in accordance with an expression:

$$H1=W1 \times (4/3).$$

12. The maxillary tooth dimension determining system according to claim 4 wherein said maxillary tooth is a maxillary first incisor having a width W1 and a height H1;
   said width W1 is determined in accordance with an expression:

$$W1=\alpha \times 2.5 \times (1/16)$$

where $\alpha$ is said pupillary distance; and
   said height H1 is determined in accordance with an expression:

$$H1=W1 \times (4/3).$$

13. A maxillary tooth dimension determining system comprising:
   still image photographing means for providing bottom still image information representing a still bottom image of a maxillary denture of a client including a portion of said denture to be treated photographed from below a face of the client;
   pupillary distance measuring means for measuring a distance between pupils of the client and providing pupillary distance information representing the measured pupillary distance;
   width determining means for determining an ideal width of said portion to be treated, from the pupillary distance information inputted thereto from said pupillary distance measuring means;
   image display means; and
   display control means for expanding or reducing bottom still image information representing a bottom still image of an ideal maxillary denture portion corresponding to said portion of the maxillary denture of the client to be treated to such an extent that the width of said ideal maxillary denture portion is equal to said determined ideal width, substituting the expanded or reduced bottom still image of said ideal maxillary denture portion for the image of said portion of the maxillary denture of the client to be treated, to thereby produce a composite image comprising said bottom still image of said maxillary denture of said client and said bottom still image of said ideal maxillary denture portion, and causing said composite image to be displayed on said image display means.

14. A maxillary tooth dimension determining system comprising:

a server apparatus, a plurality of client apparatuses, and communications links enabling communications between said server apparatus and said client apparatuses;

wherein each of said client apparatus comprises:
  still image photographing means for providing bottom still image information representing a bottom still image of a maxillary denture of a client including a portion of said denture to be treated photographed from below a face of the client; and
  pupillary distance measuring means for measuring a distance between pupils of the client and providing pupillary distance information representing the measured pupillary distance;

said client apparatus transmitting said bottom still image information and said pupillary distance information to said server apparatus through said communication links;

wherein said server apparatus comprises:
  width determining means for determining an ideal width of said portion to be treated, from the pupillary distance information transmitted from said client apparatus; and
  combining means for expanding or reducing bottom still image information representing a bottom still image of an ideal maxillary denture portion corresponding to said portion of the maxillary denture of the client to be treated to such an extent that the width of said ideal maxillary denture portion is equal to said determined ideal width, and substituting the expanded or reduced bottom still image of said ideal maxillary denture portion for the image of said portion of the maxillary denture of the client to be treated, to thereby produce a composite image comprising said bottom still image of said maxillary denture of said client and said bottom still image of said ideal maxillary denture portion;

said server apparatus transmitting said composite image information to said client apparatus through said communications links; and wherein said client apparatus further includes display means for displaying an image in accordance with said composite image information transmitted from said server apparatus.

15. A maxillary tooth dimension determining system comprising:

a server apparatus, a plurality of client apparatuses, and communications links enabling communications between said server apparatus and said client apparatuses;

wherein each of said client apparatus comprises:
  still image photographing means for providing bottom still image information representing a bottom still image of a maxillary denture of a client including a portion of said denture to be treated photographed from below a face of the client, and front still image information representing a front still image of at least a maxillary tooth of the client photographed from the front of the client's face;

said client apparatus transmitting said bottom still image information and said front still image information to said server apparatus through said communication links;

wherein said server apparatus comprises:
  dimension determining means for deriving pupillary distance information from said front still image information and determining an ideal width of the portion of the maxillary denture of the client to be treated, on the basis of the derived pupillary distance; and
  combining means for expanding or reducing bottom still image information representing a bottom still image of an ideal maxillary denture portion corresponding to said portion of the maxillary denture of the client to be treated to such an extent that the width of said ideal maxillary denture portion is equal to said determined ideal width, and substituting the expanded or reduced bottom still image of said ideal maxillary denture portion for the image of said portion of the maxillary denture of the client to be treated, to thereby produce a composite image comprising said bottom still image of said maxillary denture of said client and said bottom still image of said ideal maxillary denture portion;

said server apparatus transmitting said composite image information to said client apparatus through said communications links; and wherein said client apparatus further includes display means for displaying an image in accordance with said composite image information transmitted from said server apparatus.

16. A tooth dimension determining process comprising steps in which:

a client apparatus transmits to a server apparatus through communication links, tooth information to be used in determining an ideal dimension of a tooth of a client to be shaped, and image information representing an image of a denture including said tooth to be shaped;

said server apparatus determines the ideal dimension for said tooth to be shaped from said tooth information;

said server apparatus substitutes information representing an image of an ideal tooth having the determined ideal dimension for that part of said image information received from said client apparatus which corresponds to said tooth of said client to be shaped, to thereby produce composite image information representing a composite image comprising the image of said denture and the image of said ideal tooth;

said server apparatus transmits said composite image information to said client apparatus through said communications links; and said client apparatus uses said composite image information and provides a visual output of the composite image comprising the image of said denture and the image of said ideal tooth.

* * * * *